United States Patent [19]

Teodorescu et al.

[11] Patent Number: 5,078,970

[45] Date of Patent: Jan. 7, 1992

[54] APPARATUS FOR WITHDRAWING A LIQUID SAMPLE FROM A SAMPLE VESSEL AND TRANSFERRING IT

[75] Inventors: Mircea Teodorescu, Jamaica; Dumitru Costea, Westbrookville, both of N.Y.

[73] Assignee: Belona Laboratory Supplies and Development, Inc., Westbrookville, N.Y.

[21] Appl. No.: 546,021

[22] Filed: Jun. 28, 1990

[51] Int. Cl.$^5$ .............................................. B01L 3/02
[52] U.S. Cl. ............................. 422/100; 73/864.01; 73/864.11
[58] Field of Search ............... 422/100; 73/864.23, 73/864.24, 864.01, 864.11

[56] References Cited

U.S. PATENT DOCUMENTS

| | | | |
|---|---|---|---|
| 377,520 | 2/1888 | Hutchins | 141/352 |
| 813,256 | 2/1906 | Takaki | 73/864.11 |
| 840,986 | 1/1907 | Ackley | 222/400.8 |
| 2,223,256 | 11/1940 | Kross | 222/400.8 |
| 2,378,426 | 6/1945 | Myers | 239/373 |
| 2,431,596 | 11/1947 | Wickstrum | 222/400.8 |
| 2,538,695 | 1/1951 | Mathis | 73/864.11 |
| 2,679,337 | 5/1954 | Leach | 222/209 |
| 2,724,275 | 11/1955 | Persson | 73/864.14 |
| 2,960,868 | 11/1960 | Price | 73/864.11 |
| 3,046,556 | 7/1962 | Summers, Jr. et al. | 346/140 R |
| 3,145,876 | 8/1964 | McBrien | 346/140 R |
| 3,837,376 | 9/1974 | Brown et al. | 222/113 |
| 3,848,773 | 11/1974 | Adler et al. | 222/1 |
| 4,022,347 | 5/1977 | Nable | 222/1 |
| 4,037,464 | 7/1977 | Wenander | 73/61.4 |
| 4,119,125 | 10/1978 | Elkins | 141/11 |
| 4,192,438 | 3/1980 | Foster et al. | 222/5 |
| 4,503,012 | 3/1985 | Starr | 422/100 |
| 4,565,301 | 1/1986 | Hubbard et al. | 222/5 |
| 4,675,163 | 6/1987 | Mybeck | 422/100 |

OTHER PUBLICATIONS

"Clinical Lab Products", p. 1, Nov. 1989, vol. 18, No. 11.

Primary Examiner—Robert J. Warden
Assistant Examiner—Laura E. Collins
Attorney, Agent, or Firm—Rosen, Dainow & Jacobs

[57] ABSTRACT

A pump-type apparatus is disclosed for withdrawing liquid sample from a sample vessel without the need to open the sample vessel. The apparatus comprises a holder, a cannular having a sharp tip for piercing the closure on the sample vessel and through which pumping air is introduced into the closed vessel, a liquid withdrawal tube passing through the holder and the cannula through which liquid is removed from the vessel, and a compressible bulb which when compressed introduces air under pressure into the vessel to force liquid out of the vessel through the liquid withdrawal tube. The liquid withdrawal tube is movable so that it can be retracted into the cannula while the closure is being pierced by the cannula, and so that it may be adjusted to withdraw liquid from different liquid levels or heights in the sample vessel. A seal is provided between the holder and the liquid withdrawal tube that allows movement of the tube while sealing its exterior relative to the holder. The compressible bulb has a hole for recharging air so that the recharging air enters the sample vessel above the liquid level. A movable cover tethered to the apparatus is provided to sheath the cannula tip.

28 Claims, 2 Drawing Sheets

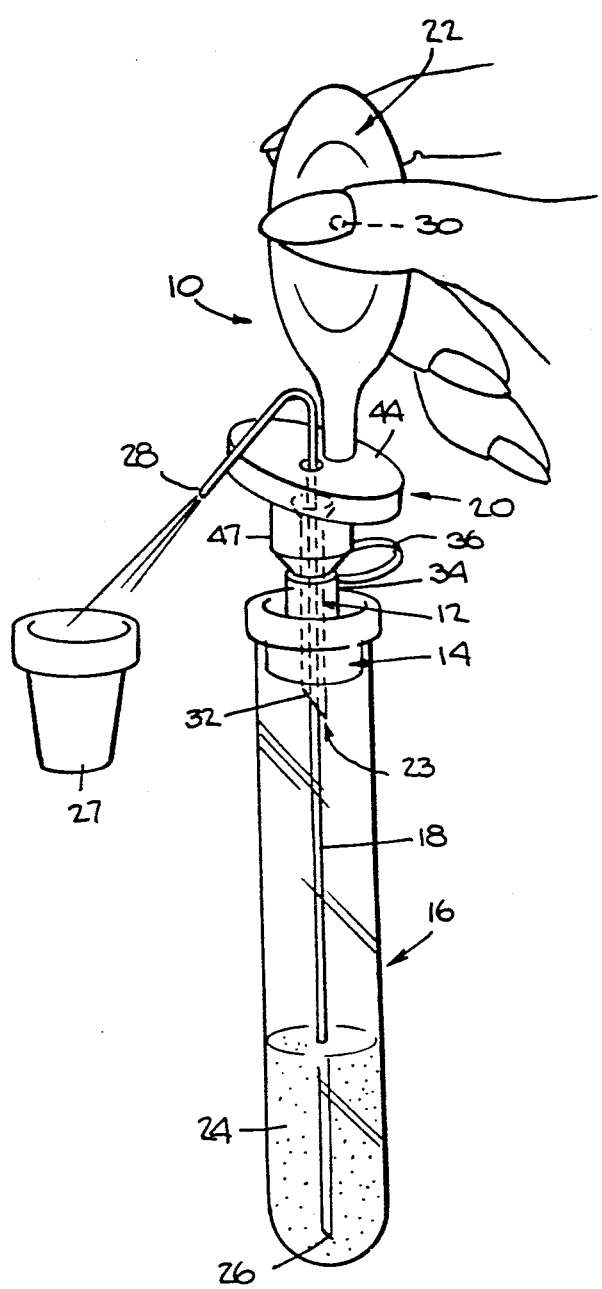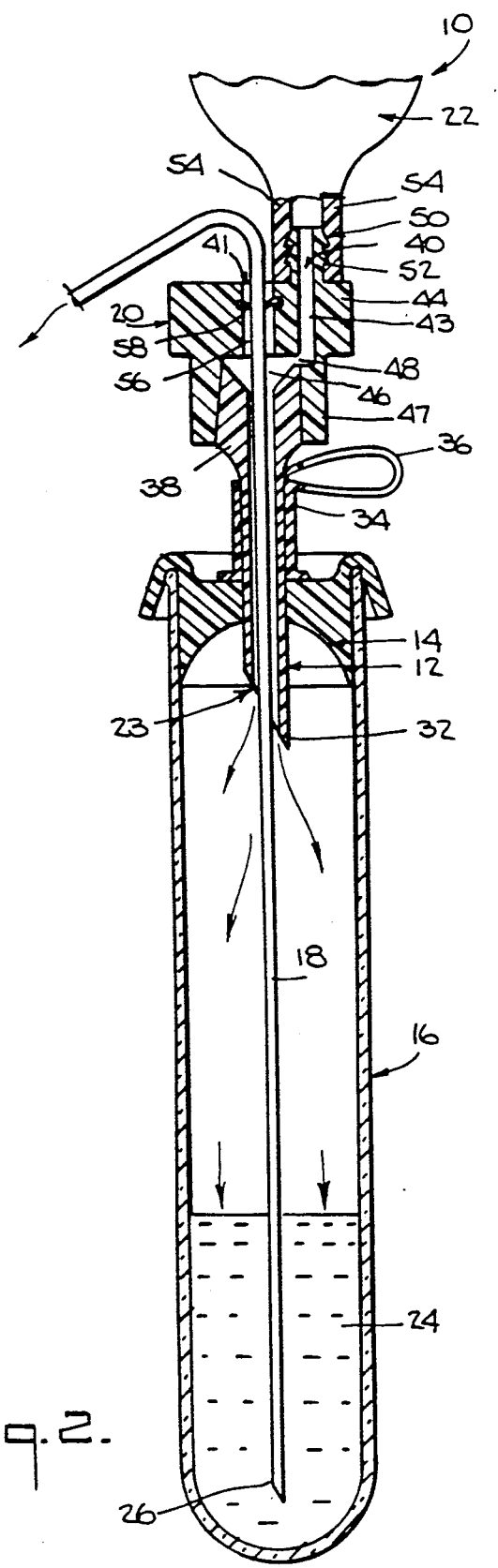
Fig. 1.
Fig. 2.

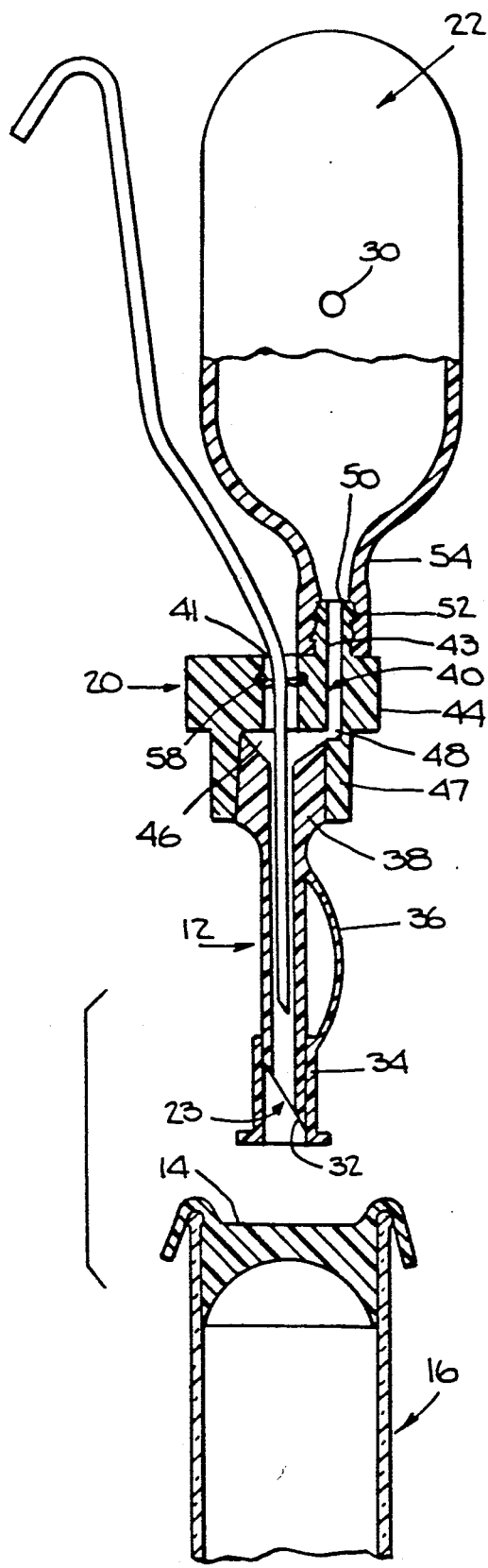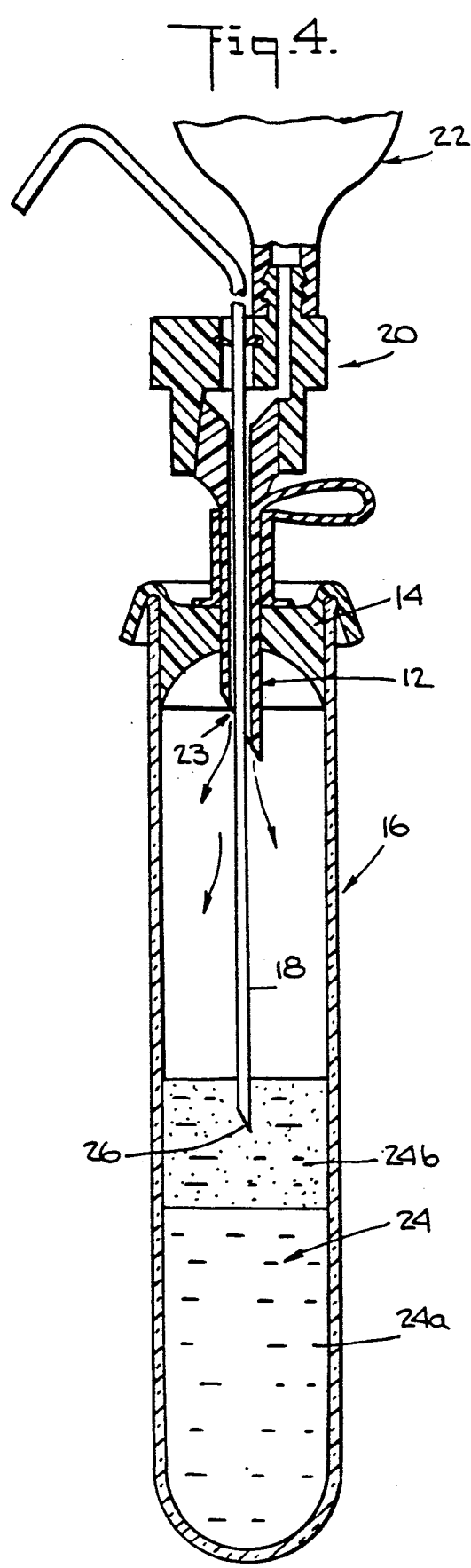

APPARATUS FOR WITHDRAWING A LIQUID SAMPLE FROM A SAMPLE VESSEL AND TRANSFERRING IT

BACKGROUND OF THE INVENTION

The invention disclosed herein relates to apparatus for withdrawing liquid samples from vessels and transferring the withdrawn liquid, particularly liquids such as body fluids or liquids which should not come into contact with personnel handling same during, for example, testing and analysis of the liquids.

Currently blood and other body fluids are routinely taken from patients for testing The sophistication of modern testing apparatus which typically include a computer enables a multitude of tests to be conducted on such body fluids Because such body fluids may contain bacteria, viruses, etc., they are typically contained in closed vessels and containers such as vials, collection tubes and the like. Frequently, during testing it is necessary for laboratory personnel to manually withdraw a small portion of such a liquid sample from a vessel. To prevent leakage or spillage of liquid from the vessel and possible contamination of laboratory personnel with the liquid, and to maintain the integrity of the liquid sample remaining in the vessel for possible further testing, it is desirable that the vessel not be opened to withdraw a portion of the liquid sample therefrom.

In addition, it is desirable that the liquid sample in the vessel be disturbed as little as possible during withdrawal of the small portion from the vessel to prevent mixing of separated components or liquid phases of the liquid sample and/or to prevent possible damage to the remaining liquid sample. This allows further testing of the remaining liquid sample, and where it is desirable to withdraw liquid from given layers of the sample, further testing may proceed without waiting for the liquid sample to settle.

An important consideration in the design, construction and use of apparatus for withdrawing such liquids is the prevention of contamination of personnel handling the apparatus and the liquid sample vessels. Thus, not only is it important that there be no leaking or escaping of sample from the apparatus and/or sample vessel during normal use of the apparatus, but the apparatus must be relatively safe to handle so it is not easy for a person handling the apparatus to be pricked by a cannula or sharp part of the apparatus.

A pump device for aspirating a liquid sample from a collection tube is described in the November, 1989 issue of "Clinical Lab Products", Vol. 18, No. 11, page 1. The pump device described in the "Clinical Lab Products" publication, according to a device inspected by the applicants, comprises two cannulas that pass through the collection tube stopper. One cannula is communicated with a bellows which when compressed introduces pumping air into the collection tube. A sample withdrawal tube is passed through the other cannula, and liquid sample is removed from the collection tube through this sample withdrawal tube. Air to recharge the bellows when compression thereof is released is sucked into the collection tube through the sample withdrawal tube, and therefore such recharging air passes through the remaining liquid sample in the collection tube and disturbs the remaining liquid in the collection tube, particularly when the bellows is operated sharply. This may be disadvantageous in certain applications such as where the liquid may settle into layers or phases and it is desired to withdraw liquid from a particular layer, or when the liquid is fragile. For example, when the liquid sample is blood, and it is desired to withdraw blood serum, air passing through the blood produces bubbles in the blood which causes the blood serum to mix with the red cells.

An additional disadvantage of the pump device inspected by the applicants is the lack of a seal between the sample withdrawal tube and the cannula which may allow contaminated liquid sample to leak or escape during normal use of the device, particularly under the action of the pumping air during pumping.

As discussed above, the person handling the liquid withdrawal apparatus should be protected against being pricked and/or against coming into contact with the liquid sample. The device described in the "Clinical Lab Products" publication, according to the device inspected by the applicants, is somewhat difficult to connect to the sample collection tube because the apparatus is difficult to grasp while applying the considerable force necessary to push the two cannulas through the stopper. As a result, the cannula tips may accidently be pushed off the stopper and prick a finger of the person connecting the device to the collator tube. Also, because that device may leak during normal use as described above, there is also a risk that the person handling the device may be contaminated by liquid sample.

OBJECTS AND SUMMARY OF THE INVENTION

It is an object of the invention disclosed herein to provide improved apparatus for withdrawing a liquid sample from a closed vessel without opening the vessel.

It is another object of the invention to provide such an apparatus which reduces the risk of liquid leaking from the vessel and the apparatus during normal use thereof.

It is another object of the invention to provide such an apparatus which withdraws the liquid sample from the vessel with minimum disturbance to the liquid remaining in the vessel.

It is another object of the invention to provide such an apparatus which reduces the risk of personnel handling the apparatus being pricked by the apparatus.

It is another object of the invention to provide such an apparatus which is adjustable so as to be able to withdraw liquid sample from different locations in the vessel, e.g., for withdrawing liquid from different layers of the liquid sample in the vessel.

It is another object of the invention to provide such an apparatus which is particularly suited for withdrawing samples of body fluids such as blood from closed vessels.

It is another object of the invention to provide such an apparatus which is inexpensive and easy to manufacture.

It is another object of the invention to provide such an apparatus which is disposable.

The above and other objects are achieved, either individually or in various combinations, in a pump-type apparatus of the type comprising a first conduit for introducing gas under pressure (e.g., air) into a closed vessel containing a liquid, and a second conduit through which the liquid is forced out of the vessel in response to the introduction therein of the gas under pressure; and in which one or more of the following is accomplished: the second conduit is movably disposed in the first conduit to facilitate passing the conduits through a closure for the vessel; the second conduit is adjusted in a leak-proof manner to withdraw liquid from different locations in the sample vessel and/or to facilitate connection of the apparatus to the vessel; the gas under pressure and recharging gas are introduced into the vessel with a minimum of disturbance to the liquid sample in the vessel, e.g., introduced above the liquid level in the vessel; all without the use of valves.

Apparatus in accordance with the invention for withdrawing liquid from a closed vessel includes the first and second conduits referred to above which each have spaced first and second openings and a holder for holding the two conduits in a given relationship to achieve given functions. Specifically, the conduits and the holder are constructed such that the second conduit passes through the first conduit intermediate the spaced openings of the second conduit, and such that the second conduit is movable relative to the first conduit while at the same time sealing is provided to prevent leakage between the second conduit and the holder. This enables the second conduit to be withdrawn into the first conduit so that a free end adjacent the first opening of the first conduit may be used to pierce the closure for the vessel, and so that the first opening in the second conduit may be positioned at a desired location in the vessel, all while preventing leakage during normal use as described above.

In a specific embodiment, an exterior portion of the second conduit is sealed with respect to the holder and the first conduit so that liquid flow past the exterior portion of the second conduit and the holder, and liquid flow from the second conduit into the first conduit, are prevented during normal operation of the apparatus while at the same time permitting movement of the second conduit.

Apparatus according to the invention is of the type in which recharging or replacement gas must flow into the apparatus after gas under pressure forces a desired amount of liquid sample out of the vessel through the second conduit to recharge the apparatus for another liquid withdrawal cycle. (While gases other than air may be used as the gas under pressure, further description herein of the invention will refer to air as the gas under pressure.) Apparatus in accordance with the invention is also constructed so that the recharging air which flows into the apparatus does not disturb the liquid sample in the vessel. In a specific embodiment, this is accomplished by introducing the recharging air into the apparatus above the liquid level in the vessel.

Apparatus according to the invention includes a means for introducing a gas under pressure into the vessel, which in a preferred embodiment comprises a manually compressible chamber communicated with the first conduit and having means for selectively communicating the chamber itself with the atmosphere. The means for selectively communicating the chamber with the atmosphere in the preferred embodiment comprises a hole in the chamber which may be selectively manually blocked. In the preferred embodiment, the compressible chamber comprises a compressible bulb having the hole therein which may be selectively manually blocked.

In the preferred embodiment, the first conduit comprises a single tubular cannula fixed to the holder and a passage in the holder. The cannula has a lumen in communication with the first passage, and the second conduit is a tubular member generally concentric with and passing through the cannula lumen. The cannula has first and second ends. The cannula first end is the free end referred to above and has an opening thereat (the first opening) through which air under pressure is introduced into the vessel. The second end of the cannula is connected to the holder with the lumen of the cannula in communication with the first passage in the holder. The cannula first end is sharp and facilitates piercing a closure on the vessel. The apparatus may comprise a cover for the cannula first end and means securing the cover to the apparatus such that the cover is moved toward the holder away from the cannula first end when the cannula first end is forced against the closure to pierce it.

In the preferred embodiment, attachment of the apparatus to the sample vessel by piercing the vessel stopper with the single cannula is relatively easy and may be accomplished with little dexterity and relatively little force. This greatly lessens the risk of pricking to persons attaching the apparatus to the vessel. Additionally, covering the cannula until the cannula tip enters the vessel stopper further reduces risk of pricking. Moreover, providing a seal for the sample withdrawal tube reduces risk of sample leakage and escape during normal use of the apparatus.

The above and other objects, aspects, features and advantages of the invention will be more readily perceived from the description of the preferred embodiments thereof taken in conjunction with the accompanying drawings and appended claims.

BRIEF DESCRIPTION OF THE DRAWINGS

The invention is illustrated by way of example and not limitation in the figures of the accompanying drawings in which like references denote the same or corresponding parts, and in which:

FIG. 1 is a perspective view of apparatus according to the invention connected to a stopped liquid sample tube showing the cannula of the apparatus passing through the sample tube stopper, and the liquid withdrawal tube of the apparatus extending through the cannula to the bottom of the liquid sample tube, and a liquid being withdrawn from the sample tube through the liquid withdrawal tube;

FIG. 2 is an axial section view taken through the liquid sample tube and part of the apparatus depicted in FIG. 1;

FIG. 3 is an exploded, axial section view of the apparatus and a portion of the sample tube depicted in FIG. 1 showing the end of liquid withdrawal tube withdrawn into the cannula with the cannula ready to pierce the sample tube stopper to connect the apparatus to the sample tube; and FIG. 4 is a view similar to that of FIG. 1 but with the end of the liquid withdrawal tube at a different location in the liquid sample tube.

DESCRIPTION OF THE PREFERRED EMBODIMENT

Referring to FIG. 1, liquid withdrawal apparatus 10 according to the invention includes a single cannula 12 (part of the first conduit), which pierces and passes through a resilient stopper or closure 14 of a liquid sample or collection tube 16, a bendable liquid withdrawal tube 18 (the second conduit), a holder 20 to which cannula 12 is attached and which establishes a relationship of cannula 12 and liquid withdrawal tube 18, and a compressible bulb 22 connected to holder 20 in communication with the lumen 23 of cannula 12.

Liquid is withdrawn by apparatus 10 from sample tube 16 according to a pumping cycle as follows. Bulb 22 is compressed to force air through lumen 23 of cannula 12 into sample tube 16, which forces liquid sample 24 in sample tube 16 to enter liquid withdrawal tube 18 through first opening 26 thereof and be discharged therefrom through second opening 28 thereof into another vessel 27. Bulb 22 is then released to start another pumping cycle. Bulb 22 includes a hole 30 therein which is covered by a person's finger when bulb 22 is compressed, and is uncovered thereafter to allow recharging air to enter bulb 22 to permit another pumping cycle. Hole 30 is preferably positioned so it can conveniently be blocked by one's finger.

Referring to FIG. 2, air under pressure from the compression of bulb 22 leaves first end 32 of cannula 12 above the level of liquid 24 in sample tube 16. Also, recharging air enters bulb 22 through hole 30 above the level of liquid 24 in sample tube 16. Thus, the compressed pumping air and recharging air do not pass through liquid 24 in sample tube 16, and thereby do not disturb liquid 24. Bulb 22 may be compressed and released gently to further avoid any disturbance to liquid 24 in sample tube 16.

As depicted in the drawings, liquid withdrawal tube 18 is movable relative to cannula 12 and holder 20, so that it may be withdrawn into cannula 12 (FIG. 3) when cannula 12 is being inserted through stopper 14 into sample tube 16, and so that opening 26 of liquid withdrawal tube 18 may be positioned at a desired height in sample tube 16 (see FIG. 4). To facilitate piercing stopper 14, the tip 32 (first end) of cannula 12 is angled to form a point. Apparatus 10 may include a cover 34 for sheathing tip 32 of cannula 12 to prevent accidental pricking of persons handling apparatus 10 prior to insertion of cannula 12 into sample tube 16. Cover 34 (FIG. 3) fits snugly about cannula 12 and is attached thereto or to holder 20 by a tether or strap 36. As tip 32 of cannula 12 enters stopper 14, cover 34 is moved along cannula 12 until cover 34 contacts an enlarged portion 38 (FIG. 2) of cannula 12 (or the point of connection of tether 36, or the holder 20 itself).

Cover 34 is made of a pliable material such as a plastic tubing, and so acts as a resilient stop for the advance of cannula 12 into stopper 14. Such a resilient stop provides an indication that cannula 12 is fully inserted, and may prevent pushing the cannula so hard into stopper 14 that the stopper may be damaged or pushed into the sample tube.

Since tip 32 of cannula 12 is covered prior to connection of apparatus 10 to sample tube 18, and since apparatus 10 may remain attached to sample tube 18 and disposed of with the sample tube, there is virtually no danger of a person being pricked by tip 32 before or after apparatus 10 is attached to sample tube 18. Moreover since apparatus 10 has only a single cannula 12, it is relatively easy to pierce the sample tube stopper with it, thereby further reducing risk of pricking to persons handling apparatus 10.

As pointed out above, liquid withdrawal tube 18 is movable with respect to cannula 12 and holder 20. This enables the location of opening 26 of liquid withdrawal tube 18 in sample tube 16 to be adjusted so that apparatus 10 may withdraw liquid from different layers 24a, 24b (FIG. 4) and different levels of the liquid sample 24 in sample tube 16. This is advantageous, for example, when extracting only serum from a blood sample.

Referring to FIG. 2, holder 20 includes first and second passages 40, 41 therein, and cannula 12 includes the enlarged diameter portion 38. First passage 40 includes a bore 43 in the top portion 44 of holder 20 and a cup-like receptacle 46 in a lower portion 47 thereof. The end 48 of bore 43 extends into the sides of receptacle 46 and thereby together they form the first passage 40 through holder 20. Receptacle 46 receives enlarged diameter portion 38 of cannula 12 therein. Enlarged diameter portion 38 of cannula 12 may be fastened to holder portion 47 in receptacle 46 by any suitable means such as an adhesive, ultrasonic welding, etc.

Projecting from the top portion 44 of holder 20 in communication with first passage 40 is a tubular extension 50 having annular ridges 52 which engage the open end 54 of bulb 22 to connect bulb 22 to holder 20. If desired bulb 22 may further be fastened to extension 52 by an adhesive or by ultrasonic welding. First passage 40 and extension 50 thereby communicate lumen 23 of cannula 12 with bulb 22. The first conduit therefore comprises lumen 23 of cannula 12, passage 40 and may also comprise extension 50.

Second passage 41 includes a bore 56 through upper portion 44 of holder 20 that is coaxial with receptacle 46 and lumen 23 of cannula 12. The remaining portion of second passage 41 is coextensive with receptacle 46 and lumen 23 of cannula 12. Thus, a portion of second passage 41 passes through and is concentric with first passage 40, and a portion of second conduit 18 passes through a portion of first conduit 12, 40, 50.

Liquid withdrawal tube 18 is inserted into second passage 41, and is movable therein, as described above. Bore 56 of first passage 41 includes an annular seal 58, which may simply be a ring of the same material that holder 20 is made of, but thin enough to be flexible and act as a squeegee or doctor blade against the outer circumference of liquid withdrawal tube 18 and form a seal there against. Seal 58 may alternatively be a ring secured in bore 56 by any suitable means. Seal 58 prevents leakage of liquid through second passage 41 while permitting liquid withdrawal tube 18 to be moved with respect to second passage 41.

Liquid withdrawal tube 18 may be a pliable plastic tube made, for example, of Teflon. Holder 20, cannula 12 and bulb 72 may be made of conventional materials which achieve the desired functions in particular environments of use, and such materials are known to those of skill in the art.

In accordance with the invention, apparatus as described herein may be made inexpensively, and consequently may be disposable even when used in large quantities.

Certain changes and modifications of the embodiments of the invention herein disclosed will be readily apparent to those of skill in the art. Moreover, uses of the invention other than for withdrawing body fluids from collection tubes will also be readily apparent to those of skill in the art. It is the applicants, intention to cover by the claims all such uses and all those changes and modifications which could be made to the embodiments of the invention herein chosen for the purposes of disclosure which do not depart from the spirit and scope of the invention.

What is claimed is:

1. Apparatus for withdrawing liquid from a vessel closed by a closure and for discharging the withdrawn liquid outside of said vessel, comprising: a holder;

a pliable tubular conduit passing through said holder for withdrawing liquid from said vessel and discharging the withdrawn liquid outside of said vessel, said tubular conduit having a first opening through which liquid in said vessel may be withdrawn from said vessel and introduced into said tubular conduit, and a second opening through which liquid introduced into said tubular conduit from said vessel may be discharged therefrom outside of said vessel;

a tubular cannula fixed to said holder and a passage in said holder, said cannula having a lumen in communication with said passage, said cannula having first and second open ends, said cannula first end being free and sharp for facilitating piercing of said closure, and said cannula second end being connected to said holder with said lumen of said cannula in communication with said passage;

said tubular conduit being generally concentric with and passing through said cannula;

means in communication with said passage of said holder for introducing a gas under pressure therein which may exit from said free end of said cannula;

said tubular conduit being movable relative to said cannula such that said second end of said tubular conduit may be moved relative to said cannula from a first position within said cannula which facilitates piercing of said closure by said cannula to a second position outside of said cannula so that said second end of said tubular conduit may be moved to a desired depth in said vessel after said cannula passes through said closure; and means for sealing an exterior portion of said tubular conduit with respect to said holder such that liquid flow past said exterior portion of said tubular conduit and said holder is prevented during normal operation of said apparatus while said tubular conduit remains selectively movable relative to said cannula.

2. The apparatus of claim 1 wherein said gas is air and said means for introducing a gas under pressure comprises a manually compressible chamber communicated with said lumen of said cannula and having means for selectively communicating said chamber with the atmosphere.

3. The apparatus of claim 2 wherein said means for selectively communicating said chamber with the atmosphere comprises a hole in said chamber which may be selectively manually blocked.

4. The apparatus of claim 3 wherein said compressible chamber comprises a compressible bulb having said hole therein which may be selectively manually blocked.

5. The apparatus of claim 1 wherein said apparatus comprises a cover for said cannula free end and means securing said cover to said apparatus such that said cover is moved toward said holder away from said cannula free end when said cannula free end is forced against said closure to pierce it.

6. Apparatus for withdrawing liquid from a vessel closed by a closure and for discharging the withdrawn liquid outside of said vessel, comprising:

a first conduit for introducing a gas under pressure into said vessel to force liquid in said vessel to enter a second conduit and to be discharged therefrom;

a pliable said second conduit for withdrawing liquid from said vessel and discharging the withdrawn liquid outside of said vessel;

a holder for holding said first and second conduits in a given relationship, said first and second conduits passing through said holder;

said second conduit having a first opening through which liquid in said vessel may be withdrawn from said vessel and introduced into said second conduit, and a second opening through which liquid introduced into said second conduit from said vessel may be discharged therefrom outside of said vessel;

said first conduit having a first opening through which said gas under pressure may be introduced therein and a second opening through which said gas under pressure may exit said first conduit into said vessel, said first conduit at said second opening being sharp for facilitating piercing of said closure;

means in communication with said first opening of said first conduit for introducing said gas under pressure therein;

said first and said second conduits and said holder being constructed and assembled such that:

(a) said second conduit passes through said first conduit intermediate said first and second openings of said second conduit;

(b) said second conduit is movable relative to said first conduit such that said second end of said second conduit may be moved relative to said first conduit from a first position within said first conduit which facilitates piercing of said closure by said first conduit to a second position outside of said first conduit so that said second end of said second conduit may be moved to a desired depth in said vessel after said first conduit passes through said closure; and (c) an exterior portion of said second conduit is sealed with respect to said holder such that liquid flow past said exterior portion of said second conduit and said holder is prevented during normal operation of said apparatus.

7. The apparatus of claim 6 wherein said gas is air and said means for introducing a gas under pressure comprises a manually compressible chamber communicated with said second opening of said first conduit and having means for selectively communicating said chamber with the atmosphere.

8. The apparatus of claim 7 wherein said means for selectively communicating said chamber with the atmosphere comprises a hole in said chamber which may be selectively manually blocked.

9. The apparatus of claim 8 wherein said compressible chamber comprises a compressible bulb having said hole therein which may be selectively manually blocked.

10. The apparatus of claim 6 wherein said first conduit comprises a tubular cannula fixed to said holder and a first passage in said holder, said cannula having a lumen in communication with said first passage, said second conduit being a tubular member generally concentric with and passing through said lumen of said cannula, said cannula having first and second ends, said cannula first end being free and constituting said first opening of said first conduit, and said second end of said cannula being connected to said holder with said lumen of said cannula in communication with said first passage.

11. The apparatus of claim 10 wherein said apparatus comprises a cover for said cannula first end and mean securing said cover to said apparatus such that said cover is moved toward said holder away from said cannula first end when said cannula first end is forced against said closure to pierce it.

12. The apparatus of claim 1 comprising another passage in said holder in communication with said lumen of said cannula, wherein said tubular conduit passes through said another passage and said lumen of said cannula with said first end of said tubular conduit outside of said another passage, wherein said another passage includes a ring therein made of the same material as said holder, said ring comprising said sealing means and sealing said exterior portion of said tubular conduit with respect to the interior of said another passage.

13. The apparatus of claim 10 wherein said holder has a second passage in communication with said lumen of said cannula, wherein said tubular member passes through said second passage and said lumen of said cannula with said first end of said second conduit outside of said second passage, wherein said exterior portion of said second conduit is an exterior portion of said tubular member, and wherein said second passage includes a ring therein made of the same material as said holder, said ring comprising said sealing means and sealing said exterior portion of said tubular member with respect to the interior of said second passage.

14. Apparatus for withdrawing liquid from a vessel closed by a closure and for discharging the withdrawn liquid outside of said vessel, comprising:
a holder;
a pliable tubular conduit passing through said holder for withdrawing liquid from said vessel and discharging the withdrawn liquid outside of said vessel, said tubular conduit having a first opening through which liquid in said vessel may be withdrawn from said vessel and introduced into said tubular conduit, and a second opening through which liquid introduced into said tubular conduit from said vessel may be discharged therefrom outside of said vessel;
a tubular cannula fixed to said holder, said cannula having a lumen, said cannula having first and second ends in communication with said lumen, said cannula first end being open and free, and sharp for facilitating piercing of said closure, and said cannula second end being connected to said holder;
said tubular conduit passing through at least a portion of said cannula including said first end of said cannula and being generally concentric at least with respect to said cannula first end;
means in communication with said lumen of said cannula for introducing a gas under pressure therein for discharge from said free end of said cannula into said vessel for forcing liquid in said vessel into said tubular conduit;
said tubular conduit being movable relative to said cannula said that said second end of said tubular conduit may be moved relative to said said cannula from a first position within said cannula which facilitates piercing of said closure by said cannula to a second position outside of said cannula so that said second end of said tubular conduit may be moved to a desired depth in said vessel after said cannula passes through said closure; and
means for sealing an exterior portion of said tubular conduit with respect to said apparatus such that liquid flow past said exterior portion of said tubular conduit and said apparatus is prevented at least when said second end of said tubular conduit is positioned past and outside of said cannula.

15. The apparatus of claim 14 wherein said gas is air and said means for introducing a gas under pressure comprises a manually compressible chamber communicated with said second opening of said cannula and having means for selectively communicating said chamber with the atmosphere.

16. The apparatus of claim 14 wherein said means for selectively communicating said chamber with the atmosphere comprises a hole in said chamber which may be selectively manually blocked.

17. The apparatus of claim 16 wherein said compressible chamber comprises a compressible bulb having said hole therein which may be selectively manually blocked.

18. The apparatus of claim 14 wherein said apparatus comprises a cover for said cannula free end and means securing said cover to said apparatus such that said cover is moved toward said holder away from said cannula free end when said cannula free end is forced against said closure to pierce it.

19. Apparatus for withdrawing liquid from a vessel closed by a closure and for discharging the withdrawn liquid outside of said vessel, comprising:
a holder;
a pliable tubular conduit passing through said holder for withdrawing liquid from said vessel and discharging the withdrawn liquid outside of said vessel, said tubular conduit having a first opening through which liquid in said vessel may be withdrawn from said vessel and introduced into said tubular conduit, and a second opening through which liquid introduced into said tubular conduit from said vessel may be discharged therefrom outside of said vessel;
a tubular cannula fixed to said holder, said cannula having a lumen, said cannula having first and second ends in communication with said lumen, said cannula first end being open and free, and sharp for facilitating piercing of said closure, and said cannula second end being connected to said holder;
said tubular conduit passing through at least a portion of said cannula including said first end of said cannula and being generally concentric at least with respect to said cannula first end;
means in communication with said lumen of said cannula for introducing a gas under pressure therein for discharge from said free end of said cannula into said vessel for forcing liquid in said vessel into said tubular conduit;
means in communication with said lumen of said cannula for introducing a gas therein which may exit from said free end thereof into said vessel for replacing liquid withdrawn from said vessel;
said tubular conduit being movable relative to said cannula such that said second end of said tubular conduit may be moved relative to said cannula from a first position within said cannula which facilitates piercing of said closure by said cannula to a second position outside of said cannula so that said second end of said tubular conduit may be moved to a desired depth in said vessel after said cannula passes through said closure; and means for sealing an exterior portion of said tubular conduit with respect to said apparatus such that liquid flow past said exterior portion of said tubular conduit and said apparatus is prevented at least when said second end of said tubular conduit is positioned past and outside of said cannula.

20. The apparatus of claim 19 wherein each said gas is air and said means for introducing a gas under pressure comprises a manually compressible chamber communicated with said lumen of said cannula, and wherein said means for introducing a gas into said lumen for replacing liquid withdrawn from said vessel comprises means for selectively communicating said chamber with the atmosphere.

21. The apparatus of claim 20 wherein said means for selectively communicating said chamber with the atmosphere comprises a hole in said chamber which may be selectively manually blocked.

22. The apparatus of claim 19 wherein said apparatus comprises a cover for said cannula free end and means securing said cover to said apparatus such that said cover is moved toward said holder away from said cannula free end when said cannula free end is forced against said closure to pierce it.

23. Apparatus for withdrawing liquid from a vessel closed by a closure and for discharging the withdrawn liquid outside of said vessel, comprising:
   a first conduit for introducing a gas under pressure into said vessel to force liquid in said vessel to enter a second conduit and to be discharged therefrom;
   a pliable said second conduit for withdrawing liquid from said vessel and discharging the withdrawn liquid outside of said vessel;
   a holder for holding said first and second conduits in a given relationship, said first and second conduits passing through said holder;
   said second conduit having a first opening through which liquid in said vessel may be withdrawn from said vessel and introduced into said second conduit, and a second opening through which liquid introduced into said second conduit from said vessel may be discharged therefrom outside of said vessel;
   said first conduit having a first opening through which said gas under pressure may be introduced therein and a second opening through which said gas under pressure may exit said first conduit into said vessel, said first conduit at said second opening being sharp for facilitating piercing of said closure;
   means in communication with said first conduit for introducing said gas under pressure therein for discharge into said vessel for forcing liquid in said vessel into said second conduit;
   means in communication with said first conduit for introducing a gas into said first conduit which may exit therefrom into said vessel for replacing liquid withdrawn from said vessel;
   said first and said second conduits and said holder being constructed and assembled such that:
   (a) said second conduit passes through said first conduit intermediate said first and second openings of said second conduit;
   (b) said second conduit is movable relative to said first conduit such that said second end of said second conduit may be moved relative to said first conduit from a first position within said first conduit which facilitates piercing of said closure by said first conduit to a second position outside of said first conduit so that said second end of said second conduit may be moved to a desired depth in said vessel after said first conduit passes through said closure; and
   (c) an exterior portion of said second conduit is sealed with respect to said holder such that liquid flow past said exterior portion of said second conduit and said holder is prevented during normal operation of said apparatus.

24. The apparatus of claim 23 wherein each said gas is air and said means for introducing a gas under pressure comprises a manually compressible chamber communicated with said second opening of said first conduit, and wherein said means for introducing a gas into said first conduit for replacing liquid withdrawn from said vessel comprises means for selectively communicating said chamber with the atmosphere.

25. The apparatus of claim 24 wherein said means for selectively communicating said chamber with the atmosphere comprises a hole in said chamber which may be selectively manually blocked.

26. The apparatus of claim 23 wherein said first conduit comprises a tubular cannula fixed to said holder, said cannula having first and second ends, said cannula first end being free and constituting said first opening of said first conduit, said cannula having a lumen in communication with said free end, said second conduit being a tubular member generally concentric with and passing through said lumen of said cannula.

27. The apparatus of claim 25 wherein cannula first end is sharp for facilitating piercing said said apparatus comprises a cover for said cannula first end and means securing said cover to said apparatus such that said cover is moved toward said holder away from said cannula first end when said cannula first end is forced against said closure to pierce it.

28. Apparatus for withdrawing liquid from a vessel closed by a closure and for discharging the withdrawn liquid outside of said vessel, comprising:
   a holder having first and second passages therethrough;
   a pliable tubular conduit passing through second passage for withdrawing liquid from said vessel and discharging the withdrawn liquid outside of said vessel, said tubular conduit having a first opening through which liquid in said vessel may be withdrawn from said vessel and introduced into said tubular conduit, and a second opening through which liquid introduced into said tubular conduit from said vessel may be discharged therefrom outside of said vessel;
   a tubular cannula fixed to said holder, said cannula having a lumen, said cannula having first and second ends in communication with said lumen, said cannula first end being open and free, and sharp for facilitating piercing of said closure, and said cannula second end being connected to said holder in communication with said first and second passages;
   said tubular conduit passing through said cannula lumen and said second end of said cannula into sand through said second passage and being generally concentric with respect to said lumen;
   means in communication with said first passage for introducing air under pressure to said lumen of said cannula for discharge from said free end of said cannula into said vessel for forcing liquid in said vessel into said conduit;
   means in communication with said first passage for introducing air into said lumen which may exit from said free end of said cannula into said vessel for replacing liquid withdrawn from said vessel;

said tubular conduit being movable relative to said cannula such that said second end of said tubular conduit may be moved relative to said cannula from a first position within said cannula which facilitates piercing of said closure by said cannula to a second position outside of said cannula so that said second end of said tubular conduit may be moved to a desired depth in said vessel after said cannula passes through said closure; and said second passage including a ring therein made of the same material as said holder for sealing an exterior portion of said tubular conduit with respect to said second passage such that liquid flow past said exterior portion of said tubular conduit and said second passage is prevented.

* * * * *